United States Patent [19]

Prada-Silva et al.

[11] Patent Number: 4,824,869

[45] Date of Patent: * Apr. 25, 1989

[54] BASE-MODIFIED METAL OXIDE CATALYSTS FOR THE CONVERSION OF SYNTHESIS GAS TO ALCOHOLS

[75] Inventors: Guillermo Prada-Silva, Wappingers Falls; Ajit K. Bhattacharya, Hopewell Junction, both of N.Y.

[73] Assignee: Texaco Inc., White Plains, N.Y.

[*] Notice: The portion of the term of this patent subsequent to Oct. 4, 2005 has been disclaimed.

[21] Appl. No.: 158,474

[22] Filed: Feb. 22, 1988

[51] Int. Cl.$^4$ .............................................. B07C 27/01
[52] U.S. Cl. ..................................... 518/714; 518/715; 518/721; 518/128; 502/200
[58] Field of Search ................ 518/714, 721, 717, 728

[56] References Cited

U.S. PATENT DOCUMENTS 4,661,525  4/1987  Grazioso et al. .................... 518/714

FOREIGN PATENT DOCUMENTS 119609  9/1984  European Pat. Off. ............ 518/714

*Primary Examiner*—Howard T. Mars
*Attorney, Agent, or Firm*—Robert A. Kulason; James J. O'Loughlin; Vincent A. Mallare

[57] ABSTRACT

A method for preparing a mixture of lower aliphatic alcohols from the reaction of carbon monoxide and hydrogen in the presence of an oxide-containing heavy metal catalyst under carbon monoxide-hydrogenation conditions in which said catalyst comprises an alumina support, at least one heavy metal oxide selected from the group of oxides consisting of molybdenum, tungsten, rhenium, optionally, a heavy metal oxide from the group of elements consisting of cobalt, iron and nickel, and an alkali or alkaline earth promotor which has been treated with a nitrogen-containing compound, or a thermally stable derivative thereof is provided.

6 Claims, No Drawings

BASE-MODIFIED METAL OXIDE CATALYSTS FOR THE CONVERSION OF SYNTHESIS GAS TO ALCOHOLS

BACKGROUND OF THE INVENTION

1. Field of the Invention

This invention broadly relates to a process for preparing aliphatic alcohols from synthesis gas and more particularly to an improved process in which a heavy metal oxide catalyst is employed to effect the hydrogenation of carbon monoxide to produce a mixture of lower aliphatic alcohols.

Lower aliphatic alcohols have been proposed as octane enhancers or as a replacement for gasoline in fueling internal combustion engines. Certain mixtures of lower aliphatic alcohols have the EPA approval for use and are currently being marketed in the United States. The lower aliphatic alcohols can be produced from domestically available non-petroleum sources and the use of these alcohols in fuel compositions can serve to lessen the nation's dependence on foreign sources of crude oil and petroleum products.

Hydrogen and carbon monoxide, or synthesis gas, a mixture of hydrogen and carbon monoxide, can be reacted to form a mixture of lower aliphatic alcohols. The synthesis gas feedstream can be produced from such non-petroleum sources as coal and biomass in well known partial oxidation reactions.

Numerous catalytic processes have been studied in attempts to provide a viable process for the production of aliphatic alcohols from synthesis gas. The early efforts were primarily directed to the production of methanol. More recently, attention has been directed to the production of higher aliphatic alcohols or a mixture of higher aliphatic alcohols with methanol. Such a mixture is highly suitable as an octane enhancing component for motor fuel and as a substitute for tetraalkyl lead additives in motor fuel.

A major problem with the synthesis gas to alcohol conversion process is the occurrence of competing reactions constantly taking place on the surface of the catalyst. Thus, even when the desired product is formed on the catalyst, some of this product may undergo further reactions with adverse effects on the yield of the desired product. It is evident that if some means could be provided for reducing or minimizing competing reactions on the catalyst surface, then improved yields of the desired product might be obtained. In accordance with this invention, a decrease in the number of surface acid sites is achieved by treatment with a thermally stable base or derivative thereof. This procedure reduces the dehydration of product alcohols on the catalyst's acid sites and this results in improved selectivity.

2. Disclosure Statement

U.S. Pat. No. 3,345,427 discloses a dehydrogenation catalyst and process in which the catalyst consists of nickel, molybdenum and alkaline metal oxides on an alumina support.

U.S. Pat. No. 4,096,164 discloses a process for reacting hydrogen and carbon monoxide in the presence of a solid catalyst comprising rhodium with molybdenum or tungsten to produce 2 carbon-atom oxygenated hydrocarbons in which ethanol is the major component.

U.S. Pat. No. 4,243,553 and U.S. Pat. No. 4,243,554 disclose a molybdenum disulfide catalyst that is useful in the water gas shift, methanation, hydrogenation and dehydrogenation processes. U.S. Pat. No. 4,607,056 and U.S. Pat. No. 4,607,055 disclose synthesis gas to alcohol processes in which the catalyst comprises molybdenum in combination with a metal from the group consisting of cobalt, iron and nickel in an oxide form with an alkali metal promoter.

EPA No. 0119609 discloses an alkali promoted molybdenum disulfide catalyst that is useful for producing aliphatic alcohols from synthesis gas. The disclosures of U.S. Pat. No. 3,345,427, U.S. Pat. No. 4,096,164, U.S. Pat. No. 4,243,553, U.S. Pat. No. 4,243,554, U.S. Pat. No. 4,607,056, U.S. Pat. No. 4,607,055 and EPA No. 0119609 are incorporated herein by reference.

SUMMARY OF THE INVENTION

It has been discovered that a mixture of carbon monoxide and hydrogen can be reacted in the presence of a treated heavy metal oxide catalyst to form a mixture of lower aliphatic alcohols. More specifically, an improved process has been discovered which employs a catalyst comprising (1) a support consisting of a member selected from the group of materials consisting of alumina, silica, titania, zirconia, lanthana and mixed metal oxides thereof, (2) at least one heavy metal oxide selected from the group consisting of molybdenum oxide, tungsten oxide and rhenium oxide, (3) optionally, a heavy metal oxide selected from the group of elements consisting of cobalt oxide, iron oxide and nickel oxide, (4) a nitrogen-containing compound, or a thermally stable derivative thereof, and (5) a promoter comprising an alkali or alkaline earth element in free or combined form.

This invention also encompasses a method for improving the selectivity of a heavy metal oxide catalyst for converting synthesis gas to alcohols wherein said catalyst is treated with a nitrogen-containing compound, or a thermally stable derivative thereof.

DETAILED EMBODIMENTS OF THE INVENTION

In accordance with this invention, synthesis gas or a mixture of carbon monoxide and hydrogen is reacted under carbon monoxide hydrogenation conditions in the presence of a catalyst comprising:

(1) a support consisting of a member selected from the group of materials consisting of alumina, silica, titania, zirconia, lanthana and mixed metal oxides thereof, (2) at least one heavy metal oxide selected from the group consisting of molybdenum oxide, tungsten oxide and rhenium oxide, (3) optionally, a heavy metal oxide selected from the group consisting of cobalt oxide, iron oxide and nickel oxide, (4) a nitrogen-containing compound, or a thermally stable derivative thereof; and (5) a promoter comprising an alkali or alkaline earth element in free or combined form.

The method for treating an oxide-containing heavy metal catalyst comprises forming (1) a support consisting of a member selected from the group of materials consisting of alumina, silica, titania, zirconia, lanthana and mixed metal oxides thereof, (2) at least one heavy metal oxide selected from the group consisting of molybdenum oxide, tungsten oxide and rhenium oxide, (3) optionally forming a heavy metal oxide selected from the group consisting of cobalt oxide, iron oxide and nickel oxide, (4) treating said heavy metal oxide or oxides with a nitrogen-containing compound or a thermally stable derivative thereof, and (5) combining an alkali or an alkaline earth metal element in free or combined form with said treated metal oxide or oxides.

In a more specific aspect of the invention, a gamma alumina support and a mixture of heavy metal oxides of molybdenum and cobalt are treated with a nitrogen-containing base, such as melamine or a thermally stable derivative thereof such as melem or melon.

Synthesis gas or a mixture of hydrogen and carbon monoxide employed in this process can be obtained by methods well known in the art. The two gas components can be provided separately and combined for the reaction or the two components can be generated simultaneously in a synthesis gas process, such as a coal gasification process. The feed gas to the alcohol process may employ the hydrogen to carbon monoxide in amounts broadly ranging from about 1 to 20 moles of hydrogen per mole of carbon monoxide. The preferred mole ratio for alcohol production is from about 1 to 5 moles of hydrogen per mole of carbon monoxide.

Heavy metal oxide catalysts suitable for the synthesis gas to alcohols process can be prepared in a number of ways. The catalyst composition may be prepared in bulk, that is, without a catalyst support or carrier. It is also common to prepare catalyst compositions using a support for the active metal components. When such a catalyst support or carrier is employed it may comprise a relatively refractory, porous, absorptive high surface area material. Conventional catalyst supports comprise materials such as alumina, silica, titania, magnesia, silica-alumina and lanthana. Catalysts comprising the noted support materials are disclosed in U.S. Pat. No. 4,098,683 and this patent is incorporated herein by reference.

A nitrogen-containing heavy metal oxide catalyst may be prepared by treating the heavy metal components with appropriate nitrogen-containing compounds. A wide variety of nitrogen compounds may be employed in the catalyst preparation. The nitrogen compound may be selected from the group consisting of urea, dimethylolurea, cyanuric acid, melamine, melam, melem or melon with melamine being preferred.

According to the present invention, a nitrogen-containing starting material may be a monomer or a dimeric, trimeric or polymeric condensation product. Structural features such as s-triazine (I) and tri-s-triazine (II) are preferred. For example:

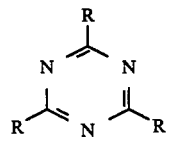

I. s-triazines e.g.,
Ia. R = NH$_2$ (melamine)
Ib. R = OH (cyanuric acid)

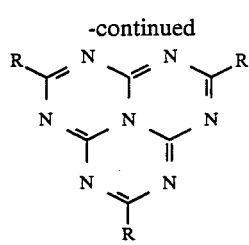

II. tri-s-triazines
IIa. R = NH$_2$(melem)

The chemistry of "s-triazines and derivatives" has been presented in great detail in "The Chemistry of Heterocyclic Compounds", Vol. 13, E. M. Smolin and L. Rapoport, Interscience Publishers Inc. (1967) and is incorporated herein by reference.

When heated above its melting point in the absence of ammonia, melamine (mp 354° C.) decomposes with loss of ammonia to afford melam (III), melem (IIa), and melon.

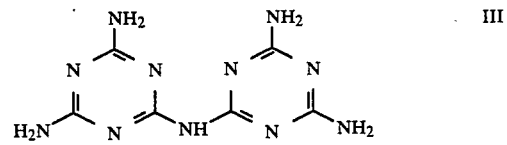

"In melamine deammonation, melam is formed first by loss of an equivalent of ammonia from two molecules of melamine. Melem is usually found together with melam and is possibly the end product of a rearrangement of melam (III).

Heating the reaction mixture at 600° C. causes further loss of ammonia with the formation of melon, a compound, or rather substance, which can survive red heat."

For the process of the present invention, a Co/Mo/Al$_2$O$_3$ catalyst is treated with a nitrogen-containing compound. Alternatively, the alumina support or a Mo/Al$_2$O$_3$ catalyst precursor can be treated at an intermediate point in the preparation of the catalyst. Samples are treated with an aqueous solution of a nitrogen-containing compound, preferably a base such as melamine. Treating is effected using a relatively dilute, aqueous solution of the nitrogen compound. In general, the aqueous preparation may contain from about 0.1 to 20 weight present of the nitrogen-containing compound with a concentration from about 0.5 to about 10 wt. % being preferred.

The mixture of the heavy metal oxide catalyst and the aqueous nitrogen-containing compound are thoroughly mixed to incorporate the nitrogen-containing compound onto the heavy metal oxide catalyst. Continuous stirring while the mixture is maintained at a moderately elevated temperature from about 50° to 60° C. for an hour or for several hours has been found effective. The treated heavy metal oxide catalyst is then separated from the mixture by filtration and dried under a vacuum. The treated heavy metal oxide catalyst is subjected to calcination. In general, calcination is effected at an elevated temperature ranging from about 300° to 700° C. while under an inert atmosphere. A preferred calcination temperature range is from about 400° to 600° C. It is preferred to conduct the calcination while passing a stream of inert gas, such as nitrogen, over the catalyst.

Following calcination, the catalyst is combined with the prescribed promoter, namely an alkali metal or an alkali earth metal element. The promoter can be combined with the heavy metal component in a variety of ways. A preferred method is by impregnation with an aqueous solution of an alkali salt, followed by drying in a vacuum oven at 120° C.

The final catalyst composition for the process of the invention may contain an amount of the thermally stable nitrogen-containing compound that will provide from about 0.01 to about 20 weight percent of nitrogen, calculated as N, based on the total weight of the catalyst. A preferred concentration of this component is from about 0.05 to about 10.0 weight percent.

In addition to the nitrogen, the final catalyst composition may contain from about 3 to about 25 wt. % of molybdenum, calculated as $MoO_3$, from about 0.3 to about 5 wt. % cobalt, calculated as CoO and from about 2 to about 12 wt. % of an alkali metal selected from the group consisting of potassium, cesium and rubidium. The balance of the catalyst consisting of a support such as gamma-alumina.

The following Examples illustrate applicants' novel process based on the use of a heavy metal oxide catalyst which has been treated with a nitrogen-containing compound.

EXAMPLE I

Base Modification of a Commercial Catalyst

A 1 percent melamine solution is prepared by dissolving 5 gr of melamine in enough deionized water to make up 500 ml of solution. The solution is heated to 50° C. and 50 grams of a commercially available Co/Mo/$Al_2O_3$ catalyst are suspended while stirring for 1 hour. The sample is filtered and dried over night in a vacuum oven at 120° C. The catalyst is subsequently calcined at 400° C. for 1 hour under nitrogen flow. This thermal treatment is done in the absence of air to prevent oxidation of the organic base. Finally, the catalyst is promoted with alkali by impregnation with an aqueous solution of potassium carbonate, followed by drying overnight in a vacuum oven at 120° C. Elemental composition corresponding to the alkali-promoted Co/Mo/$Al_2O_3$ standard (Sample A) and the base modified sample (Sample B) are compared in Table I.

EXAMPLE II

Base Modification of an Alumina Support

A 1 percent melamine solution is prepared by dissolving 5 gr of melamine in enough deionized water to make up 500 ml of solution. The solution is heated to 50° C. and 50 grams of alumina are suspended while stirring for 1 hour. The sample is filtered and dried overnight in a vacuum oven at 120° C. The support is subsequently calcined at 600° C. for 1 hour under nitrogen flow. Addition of molybdenum is carried out by incipient wetness impregnation using an aqueous solution of ammonium heptamolybdate. Drying (120° C. a vacuum oven, overnight) is followed by calcination for 3 hours at 500° C. under nitrogen flow. Cobalt is added thereafter by incipient wetness with a cobalt nitrate solution. The sample is dried as usual and calcined for 4 hours at 400° C. under nitrogen flow. Potassium is then introduced by impregnation with an aqueous solution of potassium carbonate, followed by drying overnight in a vacuum oven at 120° C. This catalyst is designated as Sample C.

EXAMPLE III

Base Modification of a Molybdenum/Alumina Precursor

Melamine modification of the molybdenum/alumina precursor followed essentially the same procedure used on the alumina support described in Example II, above, except that molybdenum was incorporated by incipient wetness prior to melamine absorption. Cobalt and potassium components were added as before. This catalyst is designated as Sample D.

Chemical analyses on base-modified catalysts prepared according to Examples II and III are presented below in Table I.

TABLE I
CATALYST COMPOSITIONS

| Catalyst | Standard Sample A | Melamine-Modified Standard Sample B |
|---|---|---|
| Mo | 6.77 | 6.74 |
| Co | 2.76 | 2.61 |
| K | 5.65 | 5.46 |
| N | — | 1.10 |

| | K/Co/Mo/$Al_2O_3$ Catalyst Prepared on a Melamine-Modified Alumina Support (Sample C) | K/Co/Mo/$Al_2O_3$ Catalyst Prepared on a Melamine-Modified Molybdenum/ Precursor (Sample D) |
|---|---|---|
| Mo | 7.23 | 7.00 |
| Co | 1.42 | 1.32 |
| K | 4.91 | 5.45 |
| N | 0.07 | 0.21 |

The effectiveness of the catalysts for converting a mixture of carbon monoxide and hydrogen to a mixture of lower aliphatic alcohols was tested in a fixed bed reactor. About 20 cc of catalyst were placed in a fixed bed reactor. The reaction conditions were 1500 psig, $H_2$:CO ratio of 2:1 and gas hourly space velocity of 10,000 hr.$^{-1}$. Catalytic performance of the melamine-modified catalysts (Samples B, C and D) is compared to the standard catalyst (Sample A) below in Table II. The data show that modification of the acid properties of the standard catalyst results in improved activity and selectivity to alcohols.

TABLE II
MELAMINE-MODIFIED ALCOHOLS CATALYSTS

| Catalyst | Standard Sample A | Melamine-Modified Standard Sample B |
|---|---|---|
| Temp. °C. | 304 | 295 |
| Alcohol Prod., g/g hr | 0.06 | 0.05 |
| Alcohol Sel. % ($CO_2$-Free Basis) | 49 | 69 |

| | K/Co/Mo/$Al_2O_3$ Catalyst Prepared on a Melamine-Modified Alumina Support (Sample C) | K/Co/Mo/$Al_2O_3$ Catalyst Prepared on a Melamine-Modified Molybdenum/ Precursor (Sample D) |
|---|---|---|
| Temp. °C. | 298 | 305 |
| Alcohol Prod., g/g hr | 0.13 | 0.14 |

TABLE II-continued

MELAMINE-MODIFIED ALCOHOLS CATALYSTS

| Catalyst | | |
|---|---|---|
| Alcohol Sel. % (CO$_2$-Free Basis) | 65 | 65 |

We claim:

1. In a method for preparing lower aliphatic alcohols where carbon monoxide and hydrogen are reacted in the presence of an oxide-containing heavy metal catalyst under carbon monoxide-hydrogenation conditions and where said catalyst comprises:
   (1) a support consisting of a member selected from the group consisting of alumina, silica, titania, zirconia, lanthana and mixed metal oxides thereof;
   (2) at least one metal oxide selected from the group consisting of molybdenum oxide, tungsten oxide, and rhenium oxide;
   (3) a heavy metal oxide selected from the group of elements consisting of cobalt oxide, iron oxide and nickel oxide; and
   (4) a promoter comprising an alkali or alkaline earth element in free or combined form;
   wherein the improvement comprises improving the selectivity to said alcohols by treating said metal oxide or oxides with a nitrogen-containing compound selected from the group consisting of urea, dimethylolurea, cyanuric acid, melamine, melam, melen and melon, or a thermally stable derivative thereof.

2. A method according to claim 1 in which said nitrogen-containing compound is melamine.

3. A method according to claim 1 in which said nitrogen-containing compound is melam.

4. A method according to claim 1 in which said nitrogen-containing compound is melem.

5. A method according to claim 1 in which said nitrogen-containing compound is melon.

6. A method according to claim 1 in which said catalyst contains from about 0.01 to about 10 wt. % nitrogen, calculated as N, from about 3 to about 25 wt. % molybdenum, calculated as MoO$_3$, from about 0.3 to about 5 wt. % cobalt, calculated as CoO and from about 2 to about 12 wt. % of an alkali metal selected from the group consisting of potassium, cesium and rubidium, and the balance consisting of a support such as gamma-alumina.

* * * * *